(12) United States Patent
Pekarske et al.

(10) Patent No.: US 8,358,590 B2
(45) Date of Patent: Jan. 22, 2013

(54) SYSTEM AND METHOD FOR DYNAMIC DATA MANAGEMENT IN A WIRELESS NETWORK

(75) Inventors: Matthew Richard Pekarske, Milwaukee, WI (US); Bruce Arnold Friedman, Jasper, GA (US); Matthew George Grubis, Milwaukee, WI (US)

(73) Assignee: General Electric Company, Schenectady, NY (US)

( * ) Notice: Subject to any disclaimer, the term of this patent is extended or adjusted under 35 U.S.C. 154(b) by 149 days.

(21) Appl. No.: 12/980,560

(22) Filed: Dec. 29, 2010

(65) Prior Publication Data

US 2012/0172671 A1 Jul. 5, 2012

(51) Int. Cl.
G06F 11/00 (2006.01)
H04J 1/16 (2006.01)
H04L 1/00 (2006.01)
H04L 12/26 (2006.01)

(52) U.S. Cl. .............. 370/252; 370/254; 370/395.42

(58) Field of Classification Search .......... 370/252–255, 370/395.42, 395.41, 395.43
See application file for complete search history.

(56) References Cited

U.S. PATENT DOCUMENTS

| | | | |
|---|---|---|---|
| 6,699,188 B2 | 3/2004 | Wessel | |
| 6,895,012 B2 * | 5/2005 | Amou et al. | 370/395.4 |
| 6,990,087 B2 | 1/2006 | Rao et al. | |
| 7,577,093 B2 | 8/2009 | Itakura et al. | |
| 7,652,993 B2 | 1/2010 | van Beek | |
| 7,773,624 B2 * | 8/2010 | Rao et al. | 370/422 |
| 2003/0110060 A1 | 6/2003 | Clementi | |
| 2004/0054263 A1 | 3/2004 | Moerman et al. | |
| 2004/0114608 A1 * | 6/2004 | Rao et al. | 370/396 |
| 2004/0170152 A1 | 9/2004 | Nagao et al. | |
| 2004/0240391 A1 | 12/2004 | Beckmoller et al. | |
| 2005/0018693 A1 * | 1/2005 | Dull | 370/396 |
| 2005/0021372 A1 | 1/2005 | Mikkelsen et al. | |
| 2005/0038680 A1 | 2/2005 | McMahon | |
| 2005/0195821 A1 | 9/2005 | Yun et al. | |
| 2005/0249164 A1 * | 11/2005 | Kwak et al. | 370/335 |
| 2007/0016443 A1 | 1/2007 | Wachman et al. | |
| 2007/0064609 A1 * | 3/2007 | Igarashi | 370/230 |
| 2007/0064735 A1 | 3/2007 | Hoo et al. | |
| 2007/0179355 A1 | 8/2007 | Rosen | |

(Continued)

FOREIGN PATENT DOCUMENTS

EP 1372306 A2 12/2003
EP 2250771 9/2009

(Continued)

OTHER PUBLICATIONS

Search Report from corresponding GB Application No. 1121756.9 Apr. 20, 2012.

(Continued)

*Primary Examiner* — Chuong T Ho
(74) *Attorney, Agent, or Firm* — Andrus, Sceales, Starke & Sawall, LLP (57) ABSTRACT

A node is configured for wireless communication with an access point according to a differentiated services control parameter. The node includes a controller configured to provide individualized control of the differentiated services control parameter setting corresponding to the node. The controller is further configured to receive data, assign a priority level to the data, and adjust the differentiated services control parameter setting for the node based on the priority level.

15 Claims, 5 Drawing Sheets

U.S. PATENT DOCUMENTS

| | | |
|---|---|---|
| 2007/0195787 A1 | 8/2007 | Alnuweiri |
| 2007/0258395 A1 | 11/2007 | Jollota et al. |
| 2007/0299863 A1* | 12/2007 | Fu et al. .................. 707/102 |
| 2008/0095124 A1 | 4/2008 | Ramos et al. |
| 2008/0144502 A1 | 6/2008 | Jackowski et al. |
| 2008/0147441 A1 | 6/2008 | Kil |
| 2008/0162181 A1 | 7/2008 | Ben-Haim et al. |
| 2008/0170499 A1 | 7/2008 | Cozens et al. |
| 2009/0063187 A1* | 3/2009 | Johnson et al. .................. 705/2 |
| 2009/0135009 A1 | 5/2009 | Little et al. |
| 2009/0303908 A1 | 12/2009 | Deb et al. |
| 2010/0069730 A1 | 3/2010 | Bergstrom et al. |
| 2010/0100391 A1 | 4/2010 | Daya et al. |
| 2010/0137693 A1 | 6/2010 | Porras et al. |
| 2010/0145736 A1 | 6/2010 | Rohwer |
| 2010/0222649 A1 | 9/2010 | Schoenberg |
| 2010/0332243 A1 | 12/2010 | Weigman et al. |
| 2010/0332250 A1 | 12/2010 | Simpson et al. |
| 2011/0019721 A1 | 1/2011 | Diener |
| 2011/0191158 A1 | 8/2011 | Kateraas et al. |
| 2011/0286331 A1* | 11/2011 | Lauer ........................... 370/235 |
| 2012/0110115 A1* | 5/2012 | Lin et al. ..................... 709/217 |
| 2012/0172671 A1 | 7/2012 | Pekarske |
| 2012/0172672 A1* | 7/2012 | Pekarske et al. ............. 600/300 |
| 2012/0172673 A1* | 7/2012 | Friedman et al. ............. 600/300 |

FOREIGN PATENT DOCUMENTS

| | | |
|---|---|---|
| WO | 03/073702 A1 | 9/2003 |
| WO | 2004036847 | 4/2004 |
| WO | 2010/101938 A1 | 9/2010 |

OTHER PUBLICATIONS

Search Report from corresponding GB Application No. 1121755.1, Apr. 3, 2012.

* cited by examiner

SYSTEM AND METHOD FOR DYNAMIC DATA MANAGEMENT IN A WIRELESS NETWORK

BACKGROUND

The present invention relates generally to communications in a wireless network and, more particularly, to the dynamic management of data in a wireless local area network (WLAN).

In certain networked environments, such as medical facility networks involving patient monitoring over WLANs, it is desirable to leverage an existing investment a common network to deploy wireless bedside and telemetry applications. However, as more and more wireless clients access the WLAN, the network may become congested, with different types of devices competing for priority on the WLAN. Such interference and increased usage from multiple devices in wireless bands degrades overall network performance and can lead to gaps in critical patient data and dropouts or delays in delivering alarms that can impact patient safety. For example, a patient-worn telemetry device set up to monitor a high-acuity patient for potentially life-threatening arrhythmia may be transmitting data on the WLAN, but may not be equipped with a local alarm to alert caregivers to a change in the patient's condition. It is critical that the patient data and alarm messages from such a device be routed to, for example, a remote central monitoring station or portable electronic device carried by a caregiver in real-time over the WLAN. There may also be multiple bedside monitors competing for access to the WLAN that, by contrast, may be equipped with local alarms to alert caregivers to a change in conditions, such that any delay in transmission of an alarm on the network may not be as critical to patient safety. Furthermore, the respective acuity levels of the various patients being monitored by the various wireless monitoring devices on the WLAN may be constantly changing, and the delay of data from a lower-acuity patient being monitored by a patient-worn telemetry device may not be as critical to patient safety as a delay of data from a higher-acuity patient. In the absence of effective means for prioritizing transmission of the patient data and alarm messages among these various devices, the more critical data may be delayed or lost.

The Institute of Electronic and Electrical Engineers (IEEE) 802.11 standard for wireless LANs is a popular mechanism for setting up networks in many industrial, office, home and medical environments. The main limitation of the legacy 802.11 is that it cannot support priority classifications to differentiate among different types of traffic. That is, every type of traffic is treated with equal fairness in the network. A newer standard called 802.11e has emerged which has prioritized traffic delivery for differentiating among traffic at different levels of criticality. The 802.11e standard achieves this by having a differentiated services control parameter in the IP layer for controlling wireless communication. For example, a six-bit Differentiated Services Code Point (DCSP) may be assigned at the IP layer and used in the MAC layer to classify and prioritize types of traffic. Using the DSCP parameter for lower and higher priority traffic classes, the higher priority traffic class is assigned shorter wait times for transmission across the WLAN. However, even though 802.11e can differentiate among traffic classes, under standard operating conditions, the 802.11e DSCP parameter is static in nature, meaning that it is not optimal under all monitoring scenarios. For example, when a change in the status or condition of a patient being monitored over a medical facility WLAN occurs, the 802.11e DSCP parameter does not adapt to those changing conditions. This makes the 802.11e DSCP default parameters unsuitable for some applications, such devices used for patient monitoring in a medical facility, where dropouts and delays in delivering alarms can impact patient safety.

Furthermore, as noted above, there may be circumstances under which the signal quality of the WLAN degrades, causing the connected data rate of wireless clients accessing the WLAN to drop. When connected at the lower data rate, it takes longer for an individual wireless client to send its data and may result in lost data, delayed alarms or gaps in waveforms. Currently, wireless clients such as medical monitoring devices may often need to transmit several different types of data, depending on the particular monitoring scenario. However, in the absence of effective means for the wireless client to manage the size of its data payload, the more critical data may be delayed or lost when interference and increased usage from multiple devices in wireless bands degrades overall network performance.

Accordingly, there is need for improved systems, devices and methods of data prioritization to increase the reliability of data transmission over WLANs and to ensure robust transmission of critical data, such as patient data in medical monitoring applications.

SUMMARY

The above-mentioned shortcomings, disadvantages and problems are addressed herein which will be understood by reading and understanding the following specification.

In an embodiment, a node is configured for wireless communication with an access point according to a differentiated services control parameter. The node includes a controller configured to provide individualized control of the differentiated services control parameter setting corresponding to the node. The controller is further configured to receive data, assign a priority level to the data, and adjust the differentiated services control parameter setting for the node based on the priority level.

In another embodiment, a network includes an access point and nodes configured for wireless communication with the access point according to a differentiated services control parameter. Each of the nodes includes a controller configured to provide individualized control of the differentiated services control parameter setting corresponding to the node. The controller is further configured to receive data, assign a priority level to the data, and adjust the differentiated services control parameter setting for the node based on the priority level.

In another embodiment, a method includes receiving data. The data is acquired using a node configured for wireless communication with an access point according to a differentiated services control parameter. The method also includes assigning a priority level to the data. The priority level is assigned by a controller configured to provide individualized control of the differentiated services control parameter setting corresponding to the node. The method also includes adjusting the differentiated services control parameter setting for the node based on the priority level.

Various other features, objects, and advantages of the invention will be made apparent to those skilled in the art from the accompanying drawings and detailed description thereof.

DETAILED DESCRIPTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
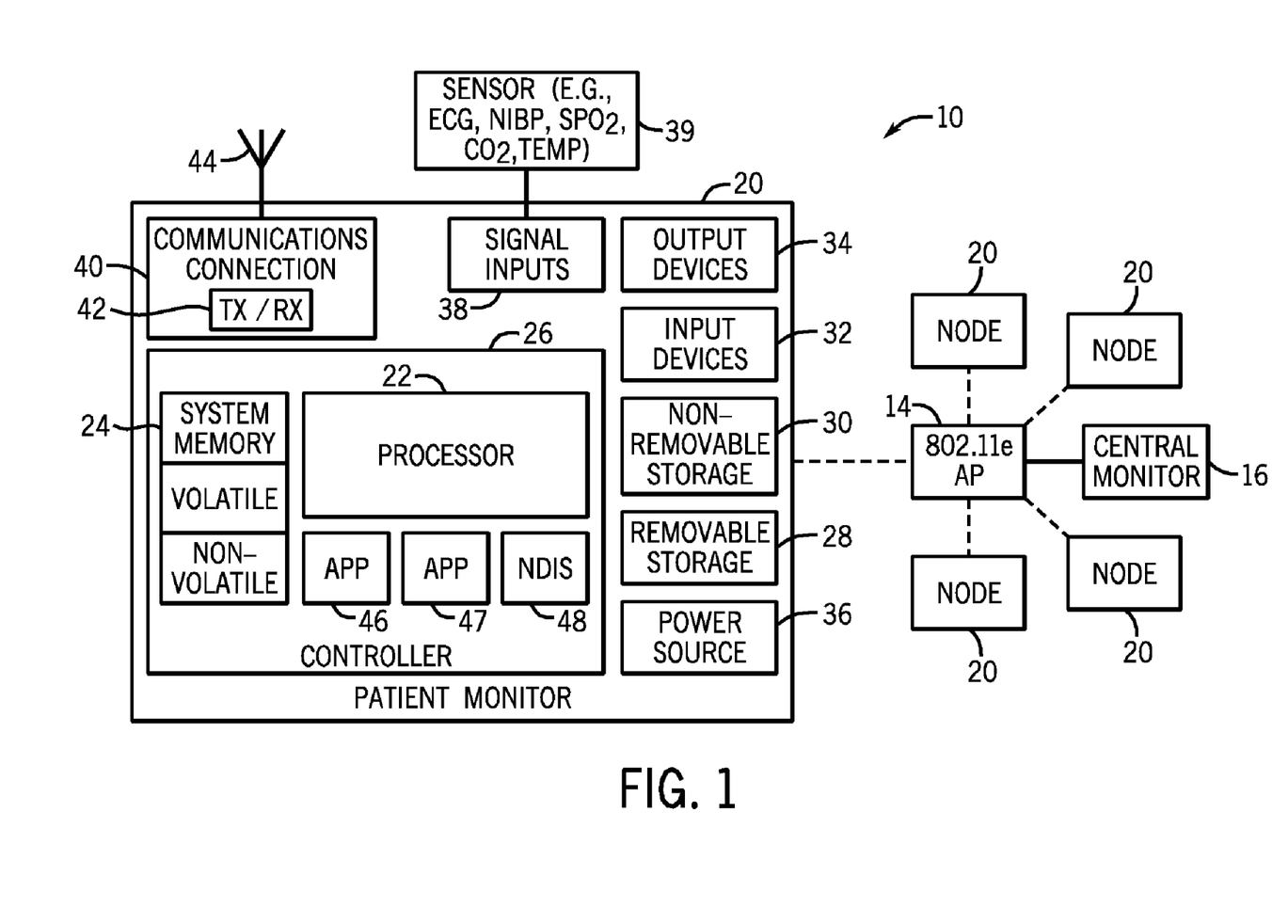
FIG. 1 is a schematic illustration of a network in accordance with an exemplary embodiment.

Referring to FIG. 1, a schematically represented network 10 is shown. Wireless network 10 is generally configured to facilitate wireless communication among two or more nodes 20, as well as other types of devices set up to access network 10. By way of example, network 10 may be a WLAN, wherein various nodes 20 are configured to communicate wirelessly over network 10 according to IEEE 802.11e protocol via one or more access points (APs) 14. Node 20 may be in a state of searching for devices that belong to network 10 by periodically scanning actively by sending probe requests and scanning for probe response signals transmitted by access point 14. Alternatively, node 20 may search passively by scanning for beacons transmitted by access point 14. According to an embodiment involving patient monitoring over a WLAN in a medical facility, network 10 may include one or more types of nodes 20 (e.g., DASH or APEX PRO monitoring devices manufactured by General Electric Company) monitoring patients of varying acuity levels. The nodes 20 may be communicating patient data to a central monitoring station 16 (e.g., a CIC PRO central monitoring station manufactured by General Electric Company) over network 10 via one or more access points 14 according to IEEE 802.11e protocol.

Node 20 is configured for access to a WLAN, such as network 10. In its most basic configuration, node 20 includes at least a processing unit 22 and a memory 24. Depending on the exact configuration and type of computing device, memory 24 may be volatile (such as RAM), non-volatile (such as ROM, flash memory, etc.) or some combination of the two. Processing unit 22 and memory 24 are included in, and form part of, a controller 26.

Node 20 may also have additional features/functionality. For example, node 20 may also include additional storage (removable and/or non-removable) including, but not limited to, magnetic or optical disks or tapes. Such additional storage is illustrated in FIG. 1 by a removable storage 28 and a non-removable storage 30. Computer storage media includes volatile and nonvolatile, removable and non-removable media implemented in any method or technology for storage of information such as computer readable instructions, data structures, program modules or other data. Node 20 may also have one or more input devices 32 such as keyboard, mouse, pen, voice input device, touch-input device, etc. One or more output devices 34 such as a display, speakers, printer, etc. may also be included. Node 20 may also be provided with a power source 36, such as a battery pack or the like. Power source 36 provides power for computations and wireless data transmissions by node 20.

Node 20 may also include analog or digital signal inputs 38. According to an embodiment wherein node 20 is a patient monitoring device, signal inputs 38 may be a data acquisition component including, for example, signal acquisition hardware (e.g., signal amplifiers, galvanic isolation components, analog-to-digital converters, etc.) and a software application executed by processing unit 22 to receive data from the signal acquisition hardware and perform further processing. In this embodiment, signal inputs 38 may be coupled to a patient by an array of sensors or transducers 39, such as, for example, electrocardiogram (ECG) leads, invasive or noninvasive blood pressure devices, temperature probes, blood gas measurement probes, and airway gas sensors in order to receive patient data.

Node 20 may also contain one or more communications connections 40 that allow node 20 to communicate with other devices. Communications connection 40 provides for communication with a WLAN via, for example, acoustic, RF, infrared and other wireless media. As discussed above, the term computer readable media as used herein includes both storage media and communication media By way of example, communications connection 40 may include a network interface card (NIC), such as a USB or SD wireless card for wirelessly communicating with different types of wireless networks. The NIC includes a transceiver 42 that is coupled to an antenna 44 for transmitting and receiving data wirelessly over a suitable frequency channel. According to an embodiment, communications connection 40 employs wireless configuration service over IEEE 802.11e wireless connections to ease network configuration, including infrastructure networks and ad hoc networks.

Communications connection 40 may also include hardware and/or software configured to evaluate the signal quality of network 10 between node 20 and, for example, access point 14. By way of example, communications connection 40 may be configured to measure a signal-to-noise ratio (SNR) for transmissions in the format of a power ratio between a signal transmitted over network 10 and background noise. Similarly, communications connection 40 may be configured to measure a received signal strength indicator (RSSI) indicative of the power present in signals transmitted over network 10. Communications connection 40 may also be configured to measure a noise floor value indicative of the lowest input signal power that can be recognized as a recoverable information signal by node 20. Communications connection 40 may also be configured to determine a retransmission rate indicative of a number of transmission retries by node 20. Communications connection 40 may also be configured to determine a number of missed beacon signals from, for example, AP 14. Other types of signal quality measurements are anticipated as well.

Referring still to FIG. 1, controller 26 includes an application 46 for processing payload data received by, acquired by or stored on node 20 in order to assign a priority level to the data packets containing the payload data. The term "payload data" as used herein generally refers to the actual information to be communicated to an end user via a data packet, such as, for example, patient parameter, alarm, waveform, device type, or location data, as opposed to header data that may be included in a data packet. The term "data" as used herein generally refers to different types of payload data unless otherwise specified. The term "payload" as used herein generally refers to the portion of a data packet containing payload data. According to an embodiment, application 46 compares this data to defined thresholds to determine a classification for the data and then performs a weighted sum calculation in order to determine the priority level. Controller 26 also includes an application 47 that assigns a differentiated services control parameter to data packets based on input from application 46. According to an embodiment, the differentiated services control parameter is a Differentiated Services Control Point (DSCP) assigned at the IP layer to data packets received from application 46. The differentiated services control parameter as defined herein, however, may include priority classifiers other than DSCP applied at other layers as well. Controller 26 also includes a network driver interface specification (NDIS) interface 48 that maintains the media access control (MAC) layer of data packets received from application 47 and controls the operation of the communications connection 40. According to an embodiment, NDIS interface 48 operates according to IEEE 802.11e protocol and uses the differentiated services control parameter to prioritize transmission of data packets via communications connection 40.

Figure 2:
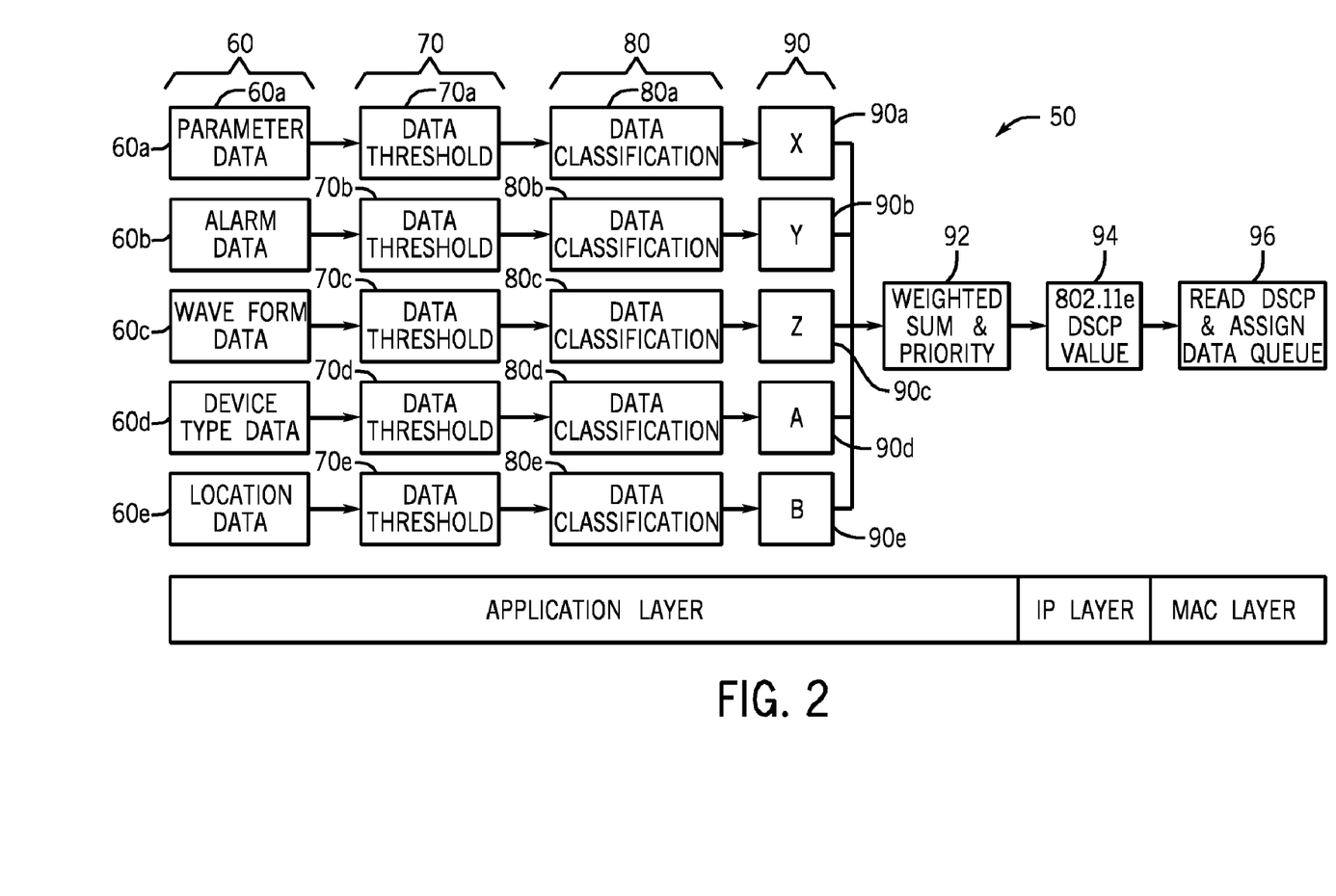
FIG. 2 is a block diagram illustrating an exemplary computer-implemented process for providing dynamic prioritization of data in the network.

Referring now to FIG. 2, a block diagram illustrating a computer-implemented process 50 for providing dynamic prioritization of data in network 10 is shown. In an embodiment, process 50 is directed to an adaptation of a differentiated services control parameter of an 802.11e implementation of a WLAN. Specifically, process 50 as illustrated in FIG. 2 provides updates to the DSCP parameter in the IP layer that determines the priority of data packets sent by node 20, where node 20 is a patient monitoring device transmitting data over a network 10 in a medical facility. An adaptive method for determining a DSCP for node 20 is desirable because the actual priority of data packets transmitted onto network 10 by node 20 may vary over time. If network 10 is congested, meaning that network 10 is busy with multiple devices attempting transmissions, a fixed DSCP value that is too low may result in dropouts and delays in delivering critical data from node 20 that can impact patient safety. Similarly, a fixed DSCP value for node 20 that is too high may lead to dropouts and delays in delivering critical data from other devices sending more critical data. Accordingly, depending on the criticality of data being transmitted by node 20 at any given time, the appropriate DSCP value for efficient data transmission can change over time.

While FIG. 2 is described and shown with respect to the adaptation of a DSCP value in an IP layer of a data packet, it is also envisioned that other or additional parameters could be modified rather than the DSCP parameter. Additionally, it is further envisioned that process 50 could be applied to other wireless communication protocols beyond 802.11e, such as updated 802.11 protocols (e.g., 802.11n). Furthermore, while FIG. 2 is described in the context of node 20 as a patient monitoring device transmitting patient data over a network 10 in a medical facility, it is envisioned that process 50 is applicable other types of nodes and networked applications.

According to an embodiment of the invention, an adaptive DSCP determination on a per-node level is implemented as a distributed type of control for a WLAN, the DSCP value defining a priority level for packet transmission that is desired for wireless transmission for that particular node 20. The controller 26 in each node 20 is configured to perform a distributed and adaptive algorithm for adapting DSCP values that works under the framework of the 802.11e standard for WLAN and uses local computations to dynamically select DSCP values to satisfy the priority requirements for that particular node 20. In the distributed control scheme, the controller 26 in each of nodes 20 in network 10 separately applies process 50 based on its individual operating conditions. That is, based on a local determination of data priority, each node determines the appropriate adaptation of its DSCP value that allows it to satisfy its own priority requirements.

Referring to FIG. 2, in process 50 at an individual node 20, controller 26 receives data to be transmitted over network 10. The data may be, for example, data acquired by node 20 or data previously stored on node 20. According to an embodiment wherein node 20 is a patient monitoring device transmitting patient data over network 10 in a medical facility, it is envisioned that the acquired data 60 may include, for example, parameter data 60a, alarm data 60b and waveform data 60c. Parameter data 60a may include, for example, discrete (e.g., digital) values of physiologic vital sign data such as heart rate or electrocardiogram (ECG) data, blood pressure data (invasive or non-invasive), temperature data, blood gas measurement data (e.g., SpO2 data), and airway gas measurement data (e.g., CO2 data). Alarm data 60b may include, for example, data indicating that certain parameter data for a patient has exceeded a predetermined limit and that assistance may be required (e.g., the patient has an excessive heart rate or temperature higher than normal body temperature). Alarm data 60b may also include data indicating a change in the state of node 20 (e.g., sensor 39 has become disconnected or power source 36 is nearly discharged). Waveform data 60c may include, for example, analog or continuous patient physiological data, such as an ECG waveform, sent at an appropriate data resolution for review by a caregiver. The data may also include, for example, device type data 60d stored on node 20 regarding the type of patient monitor (e.g., bedside monitor or telemetry device), and device location data 60e that provides an indication of where node 20 is deployed in the medical facility (e.g., intensive care unit, stepdown care unit, etc.). Other types of data may include, for example, electronic medical record (EMR) data that may be important to monitoring the patient's condition.

In the illustrated implementation of process 50 in FIG. 2, application 46 processes the data 60 received by controller 26 for transmission over network 10 and determines a priority level for the data. In particular, application 46 compares values of data 60 with a data threshold value 70 in order to determine a data classification 80 for the data. Data threshold values 70 for each type of data 60 may be established based on, for example, critical levels or ranges into which values of data 60 may fall. There may be a single data threshold value 70 for each type of data 60, or multiple data threshold values 70 establishing a range of data values for each type of data 60. According to an embodiment wherein node 20 is a patient monitoring device transmitting patient data over network 10 in a medical facility, it is envisioned that the data threshold values may be established based on the relationship between values of data 60 and patient acuity. In the illustrated embodiment, values of parameter data 60a are compared with appropriate data threshold values 70a. For example, data threshold values 70a may include user-defined limits or ranges for heart rate ECG data, blood pressure data, temperature data, blood gas measurement data and airway gas measurement data (e.g., CO2 data). Similarly, values of alarm data 60b are compared with appropriate data threshold values 70b, and values of waveform data 60c are compared with an appropriate data threshold values 70c.

Application 46 determines a data classification 80 for data 60 based on the comparison with data threshold value 70. According to an embodiment wherein node 20 is a patient monitoring device transmitting patient data over network 10 in a medical facility, it is envisioned that data classifications 80 are indicators of patient acuity based on the comparison of data 60 with data threshold value 70. For example, if data 60 includes values of heart rate parameter data 60*a* that exceed a data threshold value 70*a* for heart rate data, then application 46 may assign a data classification 80*a* indicating a high patient acuity level. If the values of heart rate parameter data 60*a* are below data threshold value 70*a* for heart rate data, then application 46 may assign a data classification 80*a* indicating a lower patient acuity level. Similarly, application 46 may assign a data classification 80*b* indicating a higher or lower acuity level depending on whether values of alarm data 60*b* exceed a data threshold value 70*b* for alarm data 60*b*. Application 46 may also assign a data classification 80*c* indicating a higher or lower acuity level depending on whether values of waveform data 60*c* exceed a data threshold value 70*c* for waveform data 60*c*. Data classifications 80*d* and 80*e* may also be assigned respectively to device type data 60*d* and device location data 60*e* based on a comparison of this data with respective data threshold values 70*d* (e.g., node 20 is above or below established size or portability constraints) and 70*e* (e.g., node 20 is inside or outside of a particular distance range).

Application 46 determines a statistical weight value 90 for values of data 60 having an assigned data classification 80. Statistical weight values 90 are used to provide a structure under which varying levels of data priority may be adaptively determined by a weighted sum calculation. According to an embodiment wherein node 20 is a patient monitoring device transmitting patient data over network 10 in a medical facility, it is envisioned that corresponding statistical weight values 90 are established for each of the various patient acuity-based data classifications 80 based on the priority to be accorded to each of these data classifications 80. By way of example, if data 60 includes values of heart rate parameter data 60*a* to be transmitted that are assigned a data classification 80*a* indicating a high patient acuity level, then application 46 determines that a corresponding statistical weight value 90*a* is appropriate. In this particular circumstance, the determined value of statistical weight value 90*a* is higher than if the values of heart rate parameter data 60*a* to be transmitted are assigned a data classification 80*a* indicating a lower patient acuity level. Statistical weight values 90*b* are established for the various alarm data classifications 80*b*, and statistical weight values 90*c* are established for the various waveform data classifications 80*c*. According to an embodiment, statistical weight values 90*b* established for alarm data classifications 80*b* may be higher than statistical weight values 90*c* established for waveform data classifications 80*c*, which in turn may be higher then statistical weight values 90*a* established for parameter data classifications 80*a*. Similarly, statistical weight values 90*d* and 90*e* are established for the various respective device type data classifications 80*d* (e.g., lower weights may be established for nodes 20 having device data classifications 80*d* as bedside monitors with local alarms, while higher weights may be established for nodes 20 having device data classifications 80*d* as telemetry devices without local alarms) and location data classifications 80*e* (e.g., higher weights may be assigned to nodes 20 having location data classifications 80*e* corresponding to an intensive care unit).

Application 46 also performs a weighted-sum calculation in order to assign an overall priority level 92 to data 60 to be transmitted by node 20 over network 10. Various types of weighted sum calculation techniques may be employed, such as linear, non-linear and geometric weighted sum calculations. The weighted sum calculation for priority level 92 factors in each of the various statistical weight values 90 assigned to the various values of data 60 to be transmitted in a data packet over network 10 and calculates an overall sum. In this way, data values 60 corresponding to high patient acuity levels will increase the overall priority level 92, and correspondingly increase the probability of the data being transmitted over network 10. Data values 60 corresponding to lower acuity levels will decrease the overall priority level 92, and correspondingly decrease the probability of the data being transmitted over network 10 and increasing the probability of transmission of higher priority data.

Application 47 receives overall priority level 92 from application 46, translates overall priority level 92 into a corresponding differentiated services control parameter value 94 (e.g., a six-bit DSCP value according to IEEE 802.11e) and assigns differentiated services control parameter value 94 to the IP layer of a data packet incorporating data 60. NDIS interface 48 receives the differentiated services control parameter value 94 and assigns the data packet to the corresponding data queue 96 at the MAC layer. The data packet incorporating data 60 is then sent to communications connection 40 for transmission to access point 14 over network 10. The data packet incorporating data 60 may then be forwarded to, for example, central monitoring station 16 for display.

Figure 3:
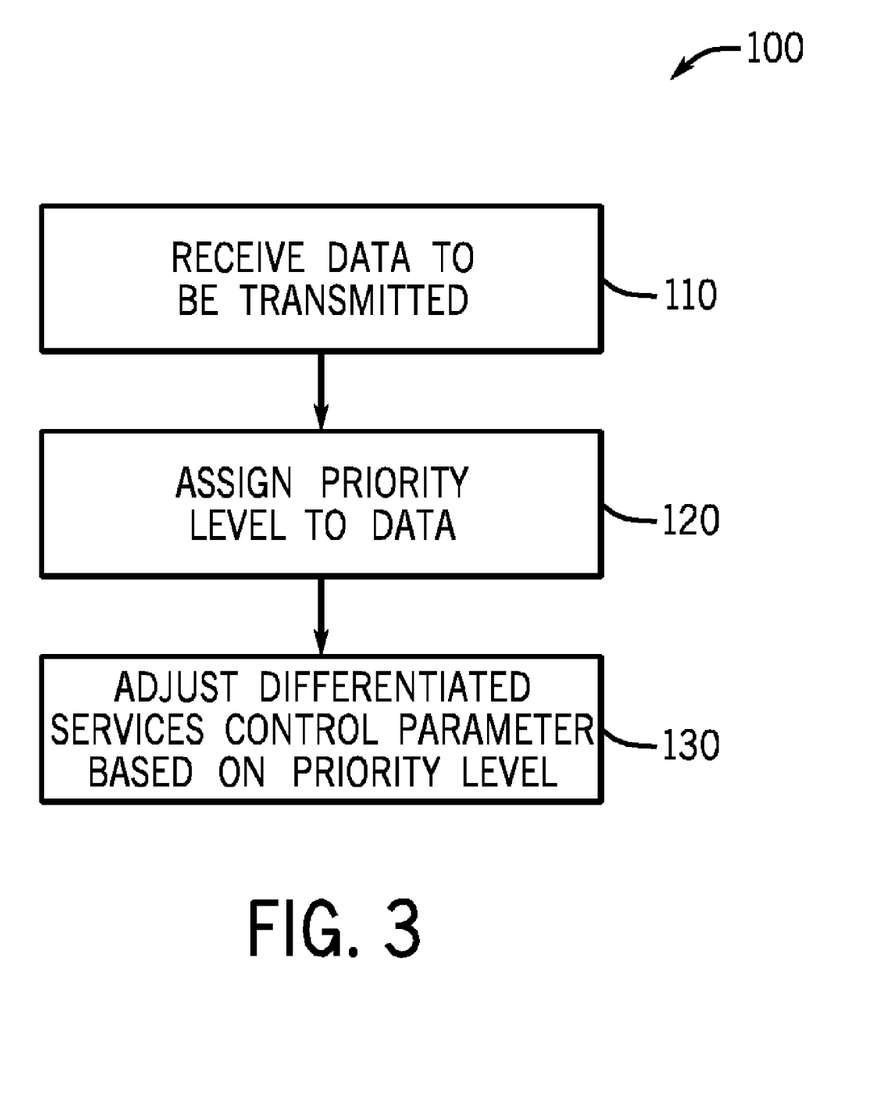
FIG. 3 is a flow chart illustrating an exemplary method in accordance with an embodiment.

Referring now to FIG. 3, a flow chart illustrating a method 100 in accordance with an embodiment is shown. Method 100 may be implemented in on, for example, the network shown in FIG. 1 and using, for example, the process described above with respect to FIG. 3. At a step 110, data to be transmitted over a network is received. According to an embodiment, the data is acquired by a node 20 configured for wireless communication with an access point 14 according to a differentiated services control parameter. The node 20 may be configured for wireless communication with the access point 14 according to IEEE 802.11e protocol, and the differentiated services control parameter may a Differentiated Services Code Point. At a step 120, a priority level is assigned to the data. The priority level may be assigned by, for example, determining a classification for the data performing a weighted sum calculation based on the classification. At a step 130, the differentiated services control parameter may be adjusted based on the priority level.

In this way, the disclosed systems and methods provide dynamic adjustment of a wireless communications protocol based on data priority in a wireless local area network. In medical monitoring applications, data is prioritized based on patient acuity, so that those patients at greatest risk would have an increased probability of their data being transmitted over the network.

Figure 4:
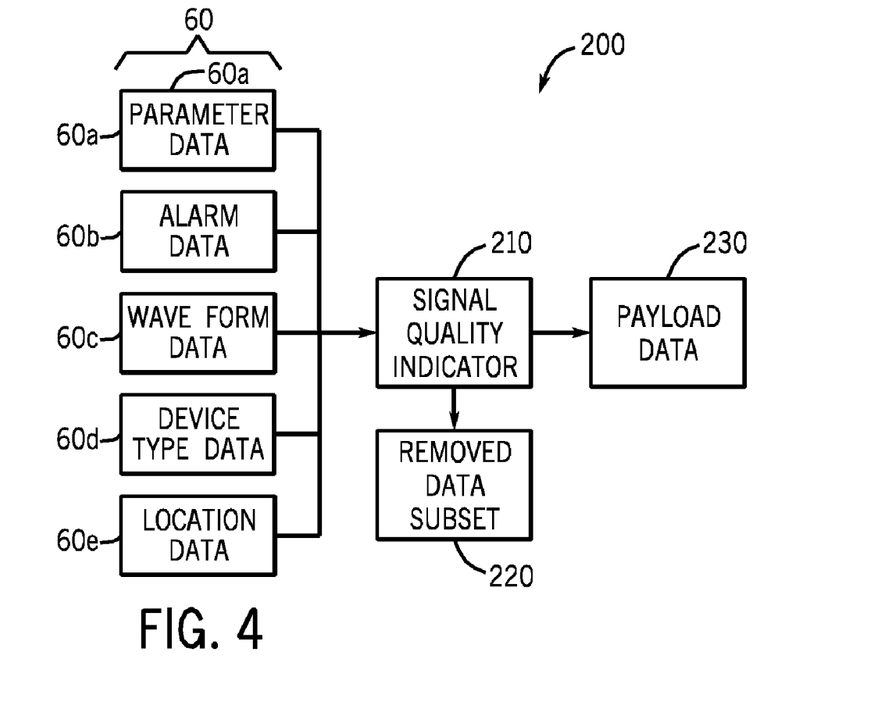
FIG. 4 is a block diagram illustrating an exemplary computer-implemented process for providing dynamic management of payload data.

Referring now to FIG. 4, a block diagram illustrating an exemplary computer-implemented process 200 for providing dynamic management of payload data is shown. In an embodiment, process 200 is directed to adjusting the amount of data included in the payload of data packets an 802.11e implementation of a WLAN. Specifically, process 200 as illustrated in FIG. 2 adjusts the amount of data included in data packets sent by node 20, where node 20 is a patient monitoring device transmitting data over a network 10 in a medical facility. An adaptive method for adjusting the amount of data included in data packets transmitted by node 20 is desirable because the signal quality of transmissions over network 10 may degrade from time to time, causing the connected data rate of nodes 20 accessing network 10 to drop. When connected at the lower data rate, it takes longer for an individual node to send its data and may result in lost data, delayed alarms or gaps in waveforms. Accordingly, depending on the signal quality of transmissions sent over network 10 at any given time, the appropriate amount of data in packets sent by node 20 for efficient data transmission can change over time.

While FIG. 4 is described and shown with respect to the adaptation of the amount of data included in the payload of a data packet based on signal quality in an 802.11 WLAN, it is also envisioned that process 200 could be applied to other wireless communication protocols beyond 802.11e, such as updated 802.11 protocols (e.g., 802.11n). Furthermore, while FIG. 4 is described in the context of node 20 as a patient monitoring device transmitting patient data over a network 10 in a medical facility, it is envisioned that process 200 is applicable other types of nodes and networked applications.

According to an embodiment of the invention, an adaptive data packet payload adjustment on a per-node level is implemented as a distributed type of control for a WLAN. The controller 26 in each node 20 is configured to perform a distributed and adaptive algorithm for adjusting the amount of data included in the payload of a data packet that works under the framework of the 802.11e standard for WLAN and uses local signal quality measurements to dynamically adjust the payload of data packets transmitted by a particular node 20. In the distributed control scheme, the controller 26 in each of nodes 20 in network 10 separately applies process 200 based on its individual operating conditions. That is, based on a local determination of signal quality, each node 20 determines the appropriate adaptation of the payload of data packets that allows it to satisfy its own requirements.

Referring to FIG. 4, in process 200 at an individual node 20, controller 26 receives data to be transmitted over network 10. As described above with respect to FIG. 2, the data may be, for example, data acquired by node 20 or data previously stored on node 20. According to an embodiment wherein node 20 is a patient monitoring device transmitting patient data over network 10 in a medical facility, it is envisioned that the acquired data 60 may include, for example, parameter data 60a, alarm data 60b and waveform data 60c. Parameter data 60a may include, for example, discrete (e.g., digital) values of physiologic vital sign data such as heart rate or electrocardiogram (ECG) data, blood pressure data (invasive or non-invasive), temperature data, blood gas measurement data (e.g., SpO2 data), and airway gas measurement data (e.g., CO2 data). Alarm data 60b may include, for example, data indicating that certain parameter data for a patient has exceeded a predetermined limit and that assistance may be required (e.g., the patient has an excessive heart rate or temperature higher than normal body temperature). Alarm data 60b may also include data indicating a change in the state of node 20 (e.g., sensor 39 has become disconnected or power source 36 is nearly discharged). Waveform data 60c may include, for example, analog or continuous patient physiological data, such as an ECG waveform, sent at an appropriate data resolution for review by a caregiver. The data may also include, for example, device type data 60d stored on node 20 regarding the type of patient monitor (e.g., bedside monitor or telemetry device), and device location data 60e that provides an indication of where node 20 is deployed in the medical facility (e.g., intensive care unit, stepdown care unit, etc.). Other types of data may include, for example, electronic medical record (EMR) data that may be important to monitoring the patient's condition.

In the illustrated implementation of process 200 in FIG. 4, application 46 also determines a signal quality indicator 210 for network 10. In particular, application 46 is configured to receive one or more signal quality measurements from communications connection 40, and to determine an overall signal quality indicator value. The signal quality measurements may be, for example, an RSSI value, a noise floor value, an SNR value, a packet retransmission rate, and a missed beacon rate as described above with reference to FIG. 1 and communications connection 40. Signal quality indicator 210 may be based on a single signal quality measurement (e.g., RSSI only), or may be derived from a combination of signal quality measurements received from communications connection 40 (e.g., RSSI and SNR).

Application 46 adjusts the amount of the data 60 received by node 20 that is included in the payload of a data packet based on signal quality indicator 210. Specifically, if signal quality indicator 210 indicates that the measured signal quality available over network 10 is less than a certain threshold value or outside of a particular range, application 46 may adjust the amount of data included in the payload of a data packet. Based on the value of signal quality indicator 210, application 46 may, for example, remove a subset of data 220 from the received data 60 by eliminating certain types of the received data 60. In an embodiment wherein node 20 is a patient monitoring device transmitting packets of patient data over network 10 in a medical facility, it is envisioned that application 46 may remove a subset of data based on whether such data is parameter data 60a, alarm data 60b, waveform data 60c, device type data 60d or location data 60e, leaving only certain types of data (e.g., alarms) to be included in the payload of a data packet. According to another embodiment, based on the value of signal quality indicator 210, application 46 may, for example, remove a subset of data 220 from the received data 60 by reducing the resolution of the received data 60. In an embodiment wherein node 20 is a patient monitoring device transmitting packets of patient data over network 10 in a medical facility, it is envisioned that application 46 may remove a subset of data by reducing the resolution of, for example, parameter data 60a, alarm data 60b, waveform data 60c, device type data 60d or location data 60e. By way of example, if signal quality indicator 210 that indicates that the measured signal quality available over network 10 is less than a certain threshold value, application 46 may reduce the resolution of ECG waveform data from 120 Hz to 60 Hz. According to another exemplary embodiment, if signal quality indicator 210 that indicates that the measured signal quality available over network 10 is less than a certain threshold value, application 46 may reduce the number of data packet retransmission attempts. Application 46 includes the remainder of the received data 60 as payload data 230 in a packet for transmission onto network 10.

Figure 5:
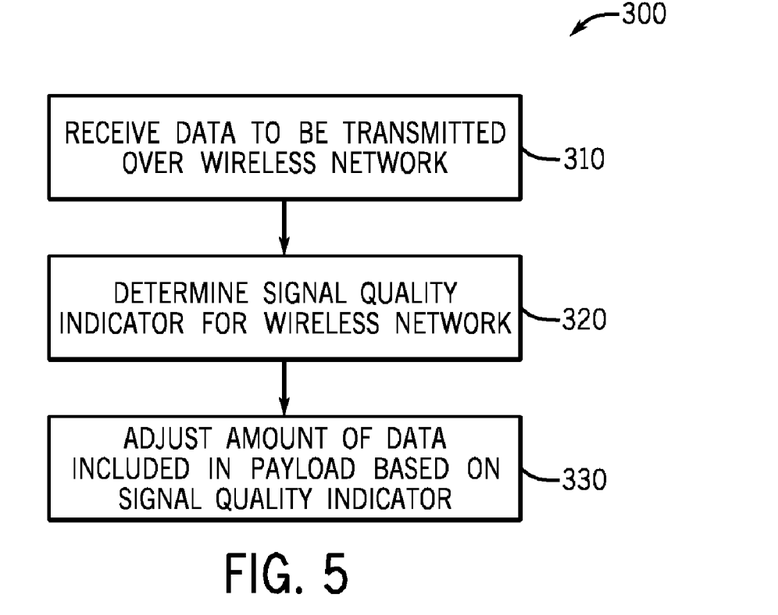
FIG. 5 is a flow chart illustrating an exemplary method in accordance with an embodiment.

Referring now to FIG. 5, a flow chart illustrating a method 300 in accordance with an embodiment is shown. Method 300 may be implemented on, for example, the network shown in FIG. 1 and using, for example, the process 200 described above with respect to FIG. 4. At a step 310, data to be transmitted over a network is received. According to an embodiment, the data is acquired by a node configured for wireless transmission of a data packet over network. The received data may include, for example, physiologic data acquired by the patient monitoring device, such as alarm data, waveform data, vital sign data, device type data, and location data. The node includes a controller configured to provide individualized control of a payload in the data packet. The node may be configured for wireless communication with the access point according to IEEE 802.11e protocol. At a step 320, a signal quality indicator is determined for the wireless network. The signal quality indicator may be based on, for example, an RSSI value, a noise floor value, an SNR ratio value, a packet retransmission rate, and a missed beacon rate. At a step 330, the amount of the data included in the payload is adjusted based on the signal quality indicator. The amount of data included in the payload may be adjusted by, for example, removing a subset of data from the received data based on the type of data, such as alarm data, waveform data, vital sign data, device type data, and location data. The amount of data included in the payload may also be adjusted by, for example, reducing the resolution of the received data.

In this way, the appropriate amount of the received data 60 included in packets sent by node 20 is dynamically adjusted for efficient data transmission depending on the signal quality of transmissions sent over network 10 at any given time. As such, the disclosed systems and methods increase the likelihood that certain types of data are not delayed or lost when interference and increased usage from multiple devices in wireless bands degrades overall network performance.

Figure 6:
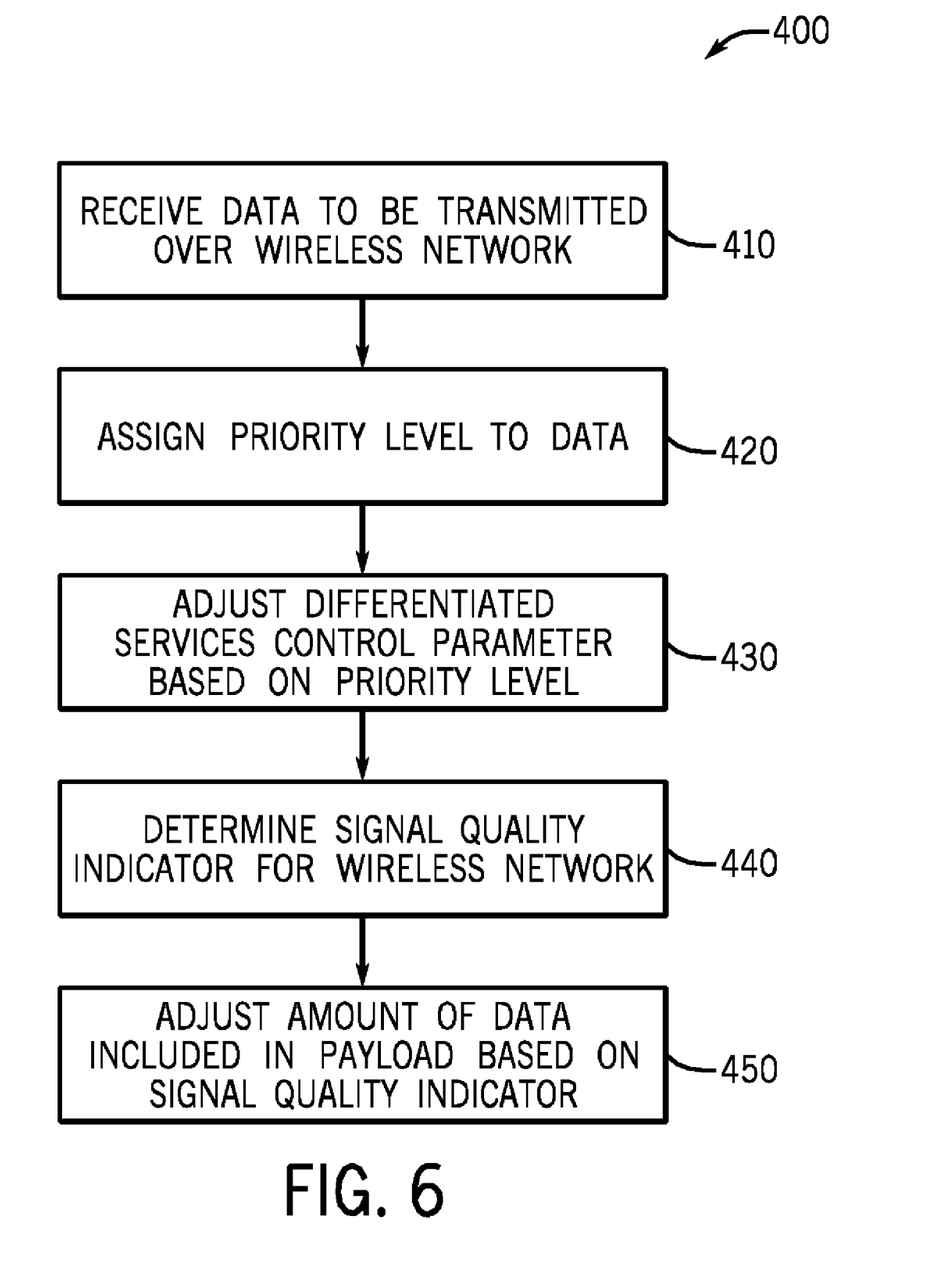
FIG. 6 is a flow chart illustrating an exemplary method in accordance with an embodiment.

Referring now to FIG. 6, a flow chart illustrating an exemplary method 400 in accordance with an embodiment is shown. In particular, FIG. 6 illustrates an implementation of a method 400 combining the processes shown and described with respect to FIG. 2 and FIG. 4 such that dynamic data management is performed based on both priority of the data to be transmitted over network 10 and the signal quality of transmissions sent over network 10 at any given time. Method 400 may be implemented in on, for example, the network shown in FIG. 1. At a step 410, data to be transmitted over a network is received. According to an embodiment, the data is acquired by a node configured for wireless communication of a data packet over a network via, for example, an access point according to a differentiated services control parameter. The node may be configured for wireless communication with the access point according to IEEE 802.11e protocol, and the differentiated services control parameter may a Differentiated Services Code Point. The received data may include, for example, physiologic data acquired by the patient monitoring device, such as alarm data, waveform data, vital sign data, device type data, and location data. At a step 420, a priority level is assigned to the data. The priority level may be assigned by, for example, determining a classification for the data performing a weighted sum calculation based on the classification. At a step 430, the differentiated services control parameter may be adjusted based on the priority level. At a step 440, a signal quality indicator is determined for the network. The signal quality indicator may be based on, for example, an RSSI value, a noise floor value, an SNR ratio value, a packet retransmission rate, and a missed beacon rate. At a step 450, the amount of the data included in the payload is adjusted based on the signal quality indicator. The amount of data included in the payload may be adjusted by, for example, removing a subset of data from the received data based on the type of data, such as alarm data, waveform data, vital sign data, device type data, and location data. The amount of data included in the payload may also be adjusted by, for example, reducing the resolution of the received data.

While the invention has been described with reference to preferred embodiments, those skilled in the art will appreciate that certain substitutions, alterations and omissions may be made to the embodiments without departing from the spirit of the invention. Accordingly, the foregoing description is meant to be exemplary only, and should not limit the scope of the invention as set forth in the following claims.

What is claimed is:

1. A node configured for wireless communication with an access point according to a differentiated services control parameter, the node comprising:
a controller configured to provide individualized control of the differentiated services control parameter setting corresponding to the node, the controller further configured to
receive data;
assign a priority level to the data;
adjust the differentiated services control parameter setting for the node based on the priority level;
perform a weighted sum calculation in order to assign the priority level to the data; and
determine a classification for the data, and to perform the weighted sum calculation based on the classification.

2. The node of claim 1 wherein the node is configured for wireless communication with the access point according to IEEE 802.11e protocol.

3. The node of claim 2, wherein the differentiated services control parameter is a Differentiated Services Code Point.

4. The node of claim 1, wherein the node is a patient monitoring device, and wherein the data is physiologic data acquired by the patient monitoring device.

5. A network comprising:
an access point; and
nodes configured for wireless communication with the access point according to a differentiated services control parameter;
wherein each of the nodes includes a controller configured to provide individualized control of the differentiated services control parameter setting corresponding to the node, the controller further configured to:
receive data;
assign a priority level to the data;
adjust the differentiated services control parameter setting for the node based on the priority level; and
determine a classification for the data, and to perform a weighted sum calculation based on the classification in order to assign the priority level to the data.

6. The network of claim 5, wherein the weighted sum calculation is one of a linear calculation, a non-linear calculation and a geometric calculation.

7. The network of claim 5 wherein the nodes are configured for wireless communication with the access point according to IEEE 802.11e protocol.

8. The network of claim 7, wherein the differentiated services control parameter is a Differentiated Services Code Point.

9. The network of claim 5, wherein one of the nodes is a patient monitoring device, and wherein the data is physiologic data acquired by the patient monitoring device.

10. The network of claim 9, wherein the physiologic data is one of alarm data, waveform data and vital sign data.

11. The network of claim 10, wherein the vital sign data is one of electrocardiogram data, blood pressure data, temperature data, blood gas measurement data, and airway gas measurement data.

12. The network of claim 11, wherein the access point is configured to transmit physiologic data received from the nodes to a central monitoring station, and wherein the central monitoring station is configured to display the physiologic data.

13. A method comprising:
receiving data, wherein the data is acquired by a node configured for wireless communication with an access point according to a differentiated services control parameter;
assigning a priority level to the data, wherein the priority level is assigned by a controller configured to provide individualized control of the differentiated services control parameter setting corresponding to the node;
adjusting the differentiated services control parameter setting for the node based on the priority level;

determining a classification for the data based by comparing the data to a threshold value; and performing a weighted sum calculation based on the classification in order to assign the priority level to the data.

14. The method of claim 13, wherein the node is configured for wireless communication with the access point according to IEEE 802.11e protocol, and wherein adjusting the differentiated services control parameter includes adjusting a Differentiated Services Code Point.

15. The method of claim 13, wherein the node is a patient monitoring device, and wherein acquiring data includes acquiring physiologic data.

* * * * *